(12) United States Patent
Sankey

(10) Patent No.: US 10,022,562 B2
(45) Date of Patent: Jul. 17, 2018

(54) RADIOTHERAPY APPARATUS

(71) Applicant: ELEKTA LIMITED, Crawley (GB)

(72) Inventor: Stephen Sankey, Brighton (GB)

(73) Assignee: ELEKTA LIMITED, Crawley (GB)

( * ) Notice: Subject to any disclaimer, the term of this patent is extended or adjusted under 35 U.S.C. 154(b) by 102 days.

(21) Appl. No.: 14/879,468

(22) Filed: Oct. 9, 2015

(65) Prior Publication Data

US 2016/0114191 A1    Apr. 28, 2016

(30) Foreign Application Priority Data

Oct. 28, 2014 (GB) .................................. 1419132.4

(51) Int. Cl.
*A61N 5/10* (2006.01)

(52) U.S. Cl.
CPC ......... *A61N 5/1049* (2013.01); *A61N 5/1071* (2013.01); *A61N 2005/1054* (2013.01); *A61N 2005/1055* (2013.01); *A61N 2005/1058* (2013.01); *A61N 2005/1061* (2013.01)

(58) Field of Classification Search
CPC .............................................. A61N 2005/1061
See application file for complete search history.

(56) References Cited

U.S. PATENT DOCUMENTS

| 8,605,857 | B1 | 12/2013 | Renner |
| 2010/0119032 | A1 | 5/2010 | Yan et al. |
| 2012/0277570 | A1* | 11/2012 | Todor ................. A61B 6/12 600/407 |
| 2013/0114784 | A1* | 5/2013 | Nioutsikou .......... A61N 5/1038 378/4 |
| 2014/0110601 | A1* | 4/2014 | Liu ..................... G01T 1/06 250/473.1 |

FOREIGN PATENT DOCUMENTS

WO    WO 2014/096993 A1    6/2014

OTHER PUBLICATIONS

International Journal of Radiation Oncology Biology Physics, vol. 73, Issue 5, Apr. 1, 2009, Van Elmpt, et al., "3D In Vivo Dosimetry Using Megavoltage Cone-Beam CT and EPID Dosimetry", pp. 1580-1587.
UK Intellectual Property Office Search Report dated Feb. 2, 2015.

\* cited by examiner

*Primary Examiner* — Dani Fox
(74) *Attorney, Agent, or Firm* — Finnegan, Henderson, Farabow, Garrett & Dunner LLP

(57) ABSTRACT

We disclose a radiotherapy apparatus with a dose verification system in which the portal image is displayed against a background of a better-quality image diagnostic image, such as a two-dimensional radiograph, an ultrasound image, or a section taken from a three-dimensional magnetic-resonance image, cone-beam CT image, or the like.

21 Claims, 6 Drawing Sheets

RADIOTHERAPY APPARATUS

CROSS-REFERENCE TO RELATED PATENT APPLICATIONS

This application claims priority from United Kingdom Patent Application No. 1419132.4, filed on Oct. 28, 2014, which is incorporated herein by reference in its entirety.

FIELD OF THE INVENTION

The present invention relates to apparatus for delivering radiotherapy.

BACKGROUND ART

Radiotherapy consists of the application of harmful radiation to lesions (such as tumours) within the body. The radiation interferes with cellular processes within the lesion and alleviates the condition. Typically, the radiation takes the form of high-energy beams of x-radiation, with photon energies usually in excess of 1 MeV.

A number of systems are provided for monitoring the radiation that is delivered, including a so-called "portal" image, which is an image created by the treatment beam, captured using a flat-panel detector after the beam has passed through and been attenuated by the patient.

However, portal images are usually of a relatively low quality, with poor contrast within soft tissue areas. This is inherent to portal imaging, since the attenuation coefficients of the materials involved are very similar at the x-ray energies used for the treatment beam. Diagnostic imagers usually use kV beams (i.e. in the 10-200 keV range) at which the attenuation coefficients of the various materials involved are more different and thus a greater degree of contrast is possible.

US2010/0119032A1 discloses a system in which kV and MV images obtained during treatment are used to reconstruct an image of the patient's anatomy. This is then compared to a predicted dose distribution based on the machine settings and parameters during the dose delivery.

SUMMARY OF THE INVENTION

Whilst the arrangement of US2010/0119032A1 ensures that the dose is displayed against an up-to-date image of the patient anatomy, it does not verify the actual dose that is delivered to the patient. Instead, it calculates an inferred dose that is the effect of the radiation that is believed to have been delivered.

The present invention therefore provides a radiotherapy apparatus comprising a source of therapeutic radiation, a first detector for the therapeutic radiation, a support for locating a patient between the source and the detector, a second detector assembly capable of deriving an internal image of the patient on the support, and a control apparatus arranged to receive the output of the detectors, wherein the control apparatus is adapted to use the output of the first detector to reconstruct a volume image representing the radiation dose delivered to the patient by the source, and display the volume image against a background of an image derived from the second detector assembly.

In this way, the portal image derived from the first detector can be displayed against the background of a better-quality image derived from the second detector assembly. As the therapeutic beam is usually quite tightly collimated around the lesion, this can provide a diagnostic-quality image on which is highlighted the area that is being irradiated. This provides useful and meaningful context for the clinician tasked with reviewing the results of treatment.

Typically, the therapeutic source will emit x-radiation with a photon energy of at least 1 MeV. A linear accelerator is often used as the source, and a flat-panel scintillation detector is suitable for detecting this radiation. The volume image will ideally represent the radiation dose by way of a "gamma image", i.e. an image showing the difference between the dose actually delivered, derived from the first detector, and a previously-determined dose that was planned to be delivered.

Reconstruction of the volume image can be achieved through standard cone-beam CT back-projection techniques, which will be familiar to those skilled in the art.

The second detector assembly can comprise a source of diagnostic radiation of lower energy than the therapeutic radiation, and a second detector for the diagnostic radiation. This can be from a separate source, or the two sources and the two detectors can each be combined into two single units.

In this case, the image derived from the second detector can be a two-dimensional radiograph. Where the two sources are not co-incident, they will usually be arranged around the patient on a rotatable gantry with an angular separation between them. The gantry rotates during treatment, to irradiate the lesion from multiple directions and thus help minimise the dose delivered to healthy tissue. Thus, the image from the second detector can be obtained at a different time to that of the image derived from the first detector. If this is timed correctly or indexed to the gantry rotation, then the radiograph and the image can be obtained along substantially co-linear directions.

Alternatively, the second detector assembly can comprise a magnetic-resonance imaging apparatus, or an ultrasound apparatus, or the like.

The image derived from the second detector can also be a section taken from a volume image created using the output of the second detector. A volume image can be obtained directly from an MRI device, or as the output of a cone-beam CT reconstruction using radiographs obtained by the second detector. The volume image may be one of a plurality of volume images created using the output of the second detector, each depicting the patient at a different phase of a breathing cycle; in that case, the apparatus can select the appropriate volume image based on analysis of the image derived from the first detector. Although the therapeutic beam is collimated around the lesion, there will usually be a margin and therefore movement of the lesion may be correlateable with the patient's breathing cycle.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
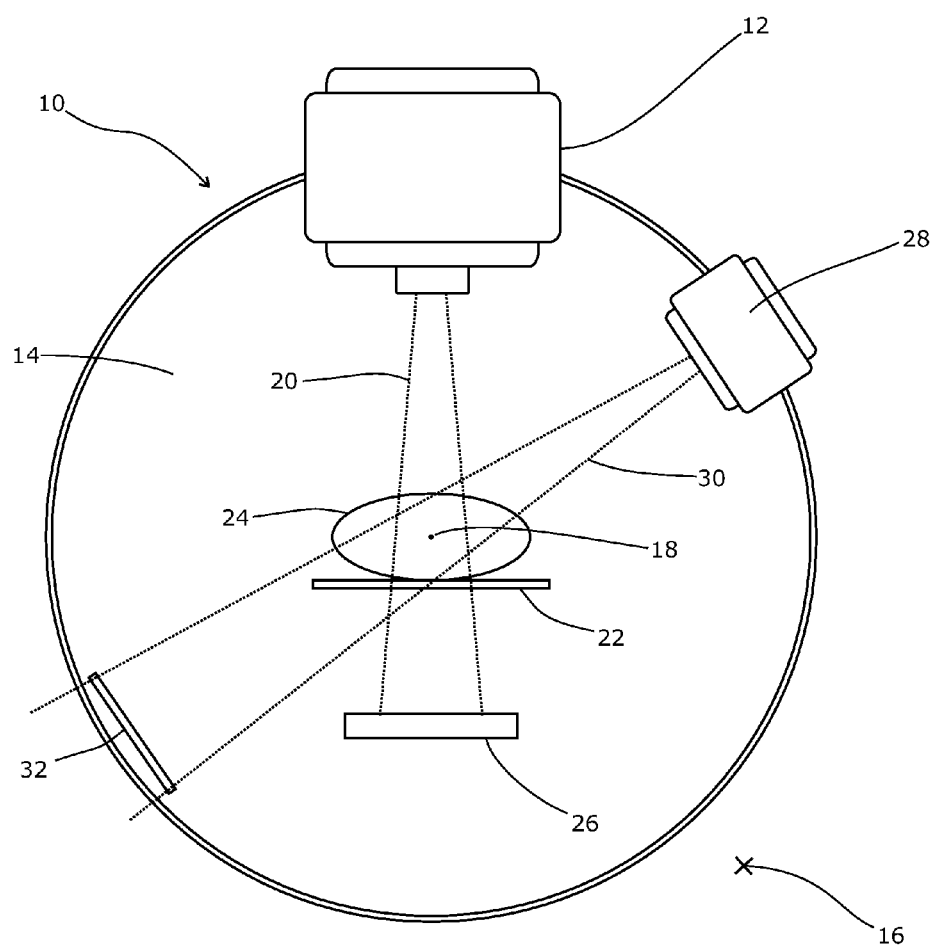
FIG. 1 shows a typical radiotherapy apparatus to which the present invention can be applied.

Referring to FIG. 1, a radiotherapy apparatus 10 includes a therapeutic source 12 which is mounted on a rotateable gantry 14. The gantry 14 is in the general form of a horizontally-arranged cylinder, set into a wall structure 16 and rotatable around the axis 18 of the cylinder, thus carrying the therapeutic source 12 with it as it rotates. The therapeutic source 12 is mounted on the end of an arm projecting from the gantry 14; the source usually comprises a linear accelerator which can be located within the arm and the gantry, with its output directed towards an x-ray target in the head section 12 to produce a beam of x-rays with an energy of about 1-5 MeV. If clinically required, the x-ray target can moved out of position to allow therapeutic use of the electron beam produced by the linear accelerator instead.

The arm and head section 12 are mounted on the gantry 14 offset from the axis 18 and with the therapeutic source 12 oriented towards the axis 18, so that the centreline of the beam 20 that it produces is co-incident with the axis 18. This then defines a point (usually known as the isocentre) which remains in the beam 20 as the gantry 14 rotates around its axis 18. Regions other than the isocentre will thus be in the beam 20 only at specific gantry angles (or ranges of gantry angles, depending on the beam width). A patient support 22 is positioned just below the isocentre, and is adjustable in three translational dimensions and two or three rotational dimensions so as to position a patient 24 lying on the support 22 with their tumour or other lesion at or close to the isocentre. In this way, a dose can be delivered to the tumour while minimising the dose delivered to healthy tissue around the tumour.

An electronic portal imaging device or EPID 26 is positioned on the gantry 14 opposite the therapeutic source 12, on the other side of the patient support 22. This comprises a scintillation detector, in a flat-panel form, which detects an image of the therapeutic x-ray beam 20 after it has been attenuated by the patient 24. This "portal" image can then be used for dosimetry purposes, i.e. monitoring the dose that was actually delivered as compared to the dose that was prescribed by the physician. The image obtained from the EPID 26 reflects the shape and intensity of the beam after attenuation; the beam shape and intensity prior to attenuation are known and the difference is therefore the dose that was actually absorbed by the patient. This can be converted to a "gamma image" or a "gamma index map" by subtracting the dose that was planned to be delivered, thereby revealing any under- or over-dosing. This needs to be reviewed by a clinician to ensure that any variations are acceptable.

Such variations may be caused by changes in the patient anatomy between the planning stage and the treatment stage, such as through movement of the patient's internal organs or by displacement due to bowel gas. However, such movements are difficult to discern in portal images and portal CT due to the poor contrast of such images in soft tissue areas. Some existing portal dosimetry solutions provide the ability to see a 2D or 3D gamma index map, with a simultaneous view of the planning CT and (optionally) the planned dose. This then provides the ability to see differences in the planning CT against the dose delivered and identify possible dosimetric discrepancies. However, subsequent movements of the patient anatomy will not be apparent, so if the dosimetric error is due to changes in patient anatomy then it will be difficult to interpret these results.

In the apparatus illustrated in FIG. 1. a diagnostic source 28 is also mounted on the gantry 14. This emits a diagnostic beam 30 towards the isocentre 18, with a significantly lower energy of about 10-200 keV suited to obtaining diagnostic-quality images. The diagnostic beam 30 is detected after attenuation by the patient 24 by a second flat-panel imager 32. A two-dimensional imager 32 can yield 2D projection images of the relevant area of the patient; these can be used directly, or several can be collated and used to reconstruct a cone-beam CT (CBCT) reconstruction of the patient. To prevent the two sources 12, 28 from obstructing each other and causing unwanted scattering, the diagnostic source 28 is mounted on the gantry offset from the therapeutic source by an angle sufficient to provide mechanical clearance between them and to place each source outside the field of the beam emitted by the other. In the example illustrated in FIG. 1, this is approximately 45° but an angle of 90° is often chosen for convenience.

Back-projection of the images from either the portal imager 26 or the diagnostic imager 32 can be achieved using standard techniques as are well-known to those skilled in the art. Examples can be found at Wendling et al, "Accurate two-dimensional IMRT verification using a back-projection EPID dosimetry method", Medical Physics 33, 259 (2006) and at Wendling et al, "A simple backprojection algorithm for 3D in vivo EPID dosimetry of IMRT treatments", Medical Physics 36, 3310 (2009).

Intrafraction imaging using the images from the diagnostic beam performed in conjunction with in-vivo portal dosimetry would provide a treatment-time view of the anatomy. The ability to simultaneously view a 2D image or a 3D or 4D intra-fraction CBCT with a 2D or 3D gamma index map would allow for better interpretation of the results. In the example discussed above, this will show the presence of bowel gas and explain the dosimetric difference in this region, allowing the clinician to reach an informed opinion.

We envisage several ways in which this can be achieved via the present invention using the apparatus of FIG. 1. A simple approach is to retain the most recent set of projection images taken by the diagnostic apparatus 28, 32 and display the image derived from the EPID 26 over a background of the image in the set which was taken along the same gantry angle. Note that the image derived from the EPID 26 may be the actual attenuated image, or the dose pattern (i.e. the unattenuated image that would have been created by the beam as emitted, minus the actual attenuated image), or the gamma plot (i.e. the dose pattern minus the planned dose). Thus, the selected background image will have a small time delay relative to the image from the EPID 26, but this will be very small compared to that of the planning CT and will give a much more accurate basis for assessment by the clinician.

An alternative is to use the projection images obtained from the diagnostic apparatus 28, 32 to reconstruct a CBCT volume image, and then obtain a 2D image from the volume image that is a view along substantially the same direction as the EPID image in question. That 2D image may be a 2D planar section (or "slice") from the CBCT volume, or a reconstructed projection image obtained from the volume. In this way, the CBCT volume will include information from more recent projection images, and the choice of 2D image will be more flexible as there will be no specific need for there to have been a projection image taken from the actual current gantry angle of the therapeutic source 12.

Where there is a CBCT volume image, this could of course be compared with a portal CT volume image (of the patient, the dose or of the gamma plot).

In a further alternative, the projection images obtained by the diagnostic apparatus 28, 32 can be grouped according to breathing phase, for example as taught in our earlier patent application WO2004/066211, to create a 4-dimensional CBCT volume image—i.e. a series of volume images being snapshots of the patient at different points in their breathing cycle. The most relevant snapshot can then be selected based on an analysis of either the EPID image, or a concurrent projection image, or both.

Figure 2:
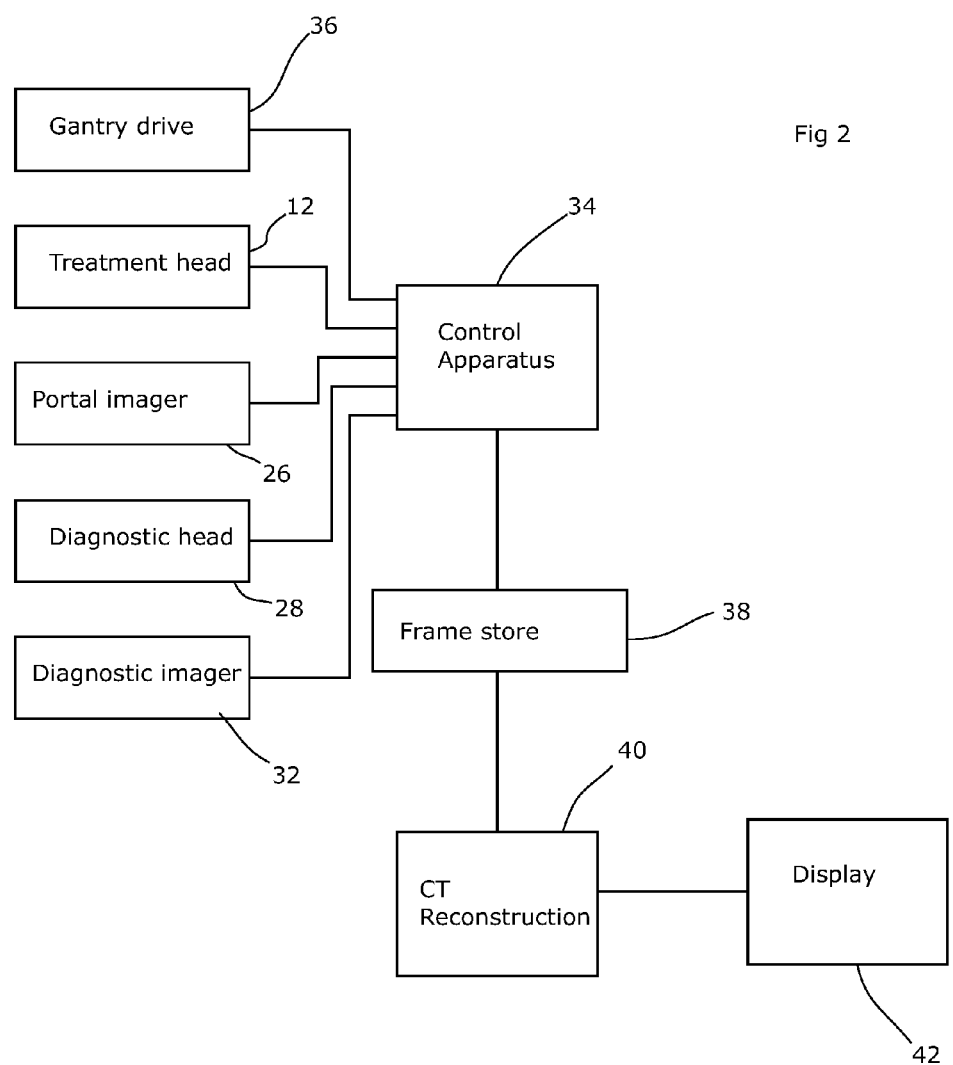
FIG. 2 shows a schematic functional structure for the apparatus of FIG. 1.

FIG. 2 shows a schematic control layout for achieving this. A control apparatus 34 sends movement instructions to the gantry drive 36 and beam & collimator instructions to the treatment head 12. It receives feedback from both in order to verify that the correct movements (etc) have been performed. Beam instructions are sent to the diagnostic head 28, and image capture instructions are sent to the diagnostic imager 32 and the portal imager 26. Images are received from the two imagers 26, 32 and are placed in an image store 38. A CT reconstruction computer 40 has access to the image store 38 and can produce CBCT volumes based on the images from the diagnostic imager 32 and portal CT volumes based on the images from the portal imager 26. Prior to reconstruction or portal CT images, the CT reconstruction computer 40 may be programmed to convert the portal images to dose images or gamma images, or the portal CT may be converted subsequent to reconstruction. The resulting volumes, and images selected from them, can be displayed via a display 42 connected to the CT reconstruction computer 40.

Figure 3:
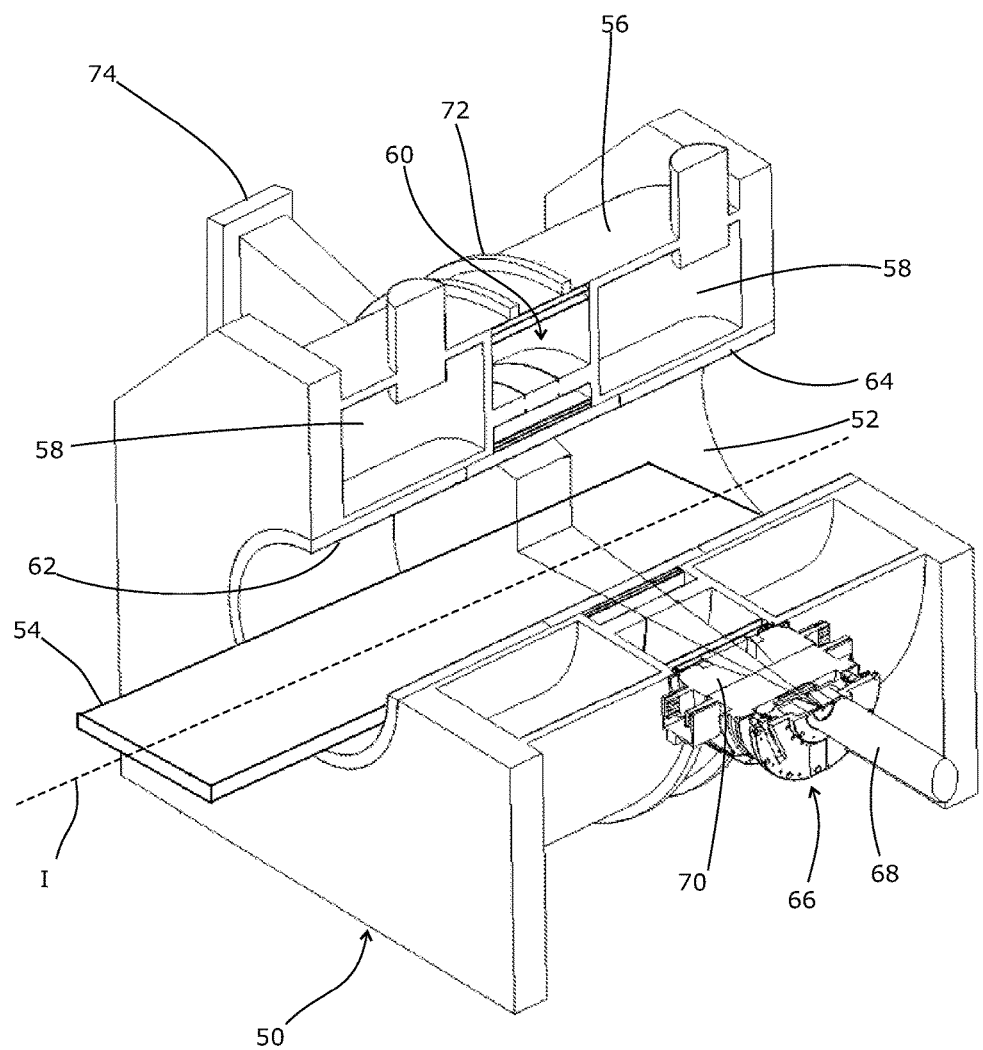
FIG. 3 shows a radiotherapy apparatus incorporating an MRI scanning function.

FIG. 3 shows an embodiment of the invention arranged around the use of a combined radiotherapy apparatus and MRI scanner. MRI scanning is generally preferable to CT scanning for the investigation of soft-tissue structures, as it gives better contrast between soft tissue types and involves a lower background dose for the patient. To allow the combination of MRI and radiotherapy, the apparatus 50 comprises a central bore 52 into and out of which a patient support couch 54 can be selectively translated. As before, the couch 54 is adjustable in three translational directions and three rotational directions to allow a patient on the couch 54 to be positioned accurately relative to the apparatus, but can is also movable by a greater distance along a horizontal, translation axis (labelled "I"), such that a patient resting on the couch is moved into and out of the radiotherapy and MRI apparatus. In one embodiment, the couch 54 is rotatable around a central vertical axis of rotation, transverse to the translation axis, although this is not illustrated. The couch 54 may form a cantilever section that projects away from a support structure (not illustrated). In one embodiment, the couch 54 is moved along the translation axis relative to the support structure in order to form the cantilever section, i.e. the cantilever section increases in length as the couch is moved and the lift remains stationary. In another embodiment, both the support structure and the couch 54 move along the translation axis, such that the cantilever section remains substantially constant in length, as described in our earlier patent application published as WO 2009/007737, the contents of which are incorporated by reference and to which the skilled person is referred for a full understanding of the described embodiment.

As mentioned above, the system 50 also comprises an MRI apparatus 56, for producing near real-time imaging of a patient positioned on the couch 54. The MRI apparatus includes a primary magnet 58 which acts to generate the so-called "primary" magnetic field for magnetic resonance imaging. That is, the magnetic field lines generated by operation of the magnet 58 run substantially parallel to the central translation axis I. The primary magnet 58 consists of one or more coils with an axis that runs parallel to the translation axis I. The one or more coils may be a single coil or a plurality of coaxial coils of different diameter. In one embodiment (illustrated), the one or more coils in the primary magnet 58 are spaced such that a central window 60 of the magnet 58 is free of coils. In other embodiments, the coils in the magnet 58 may simply be thin enough that they are substantially transparent to radiation of the wavelength generated by the radiotherapy apparatus. The magnet 58 may further comprise one or more active shielding coils, which generates a magnetic field outside the magnet 58 of approximately equal magnitude and opposite polarity to the external primary magnetic field. The more sensitive parts of the system 50, such as the accelerator, are positioned in this region outside the magnet 58 where the magnetic field is cancelled, at least to a first order.

The MRI apparatus 56 further comprises two gradient coils 62, 64, which generate the so-called "gradient" magnetic field that is superposed on the primary magnetic field. These coils 62, 64 generate a gradient in the resultant magnetic field that allows spatial encoding of the protons so that their position can be determined, for example the gradient coils 62, 64 can be controlled such that the imaging data obtained has a particular orientation. The gradient coils 62, 64 are positioned around a common central axis with the primary magnet 58, and are displaced from one another along that central axis. This displacement creates a gap, or window, between the two coils 62, 64. In an embodiment where the primary magnet 58 also comprises a central window 60 between coils, the two windows are aligned with one another.

An RF system causes the protons to alter their alignment relative to the magnetic field. When the RF electromagnetic field is turned off the protons return to the original magnetization alignment. These alignment changes create a signal which can be detected by scanning. The RF system may include a single coil that both transmits the radio signals and receives the reflected signals, dedicated transmitting and receiving coils, or multi-element phased array coils, for example. Control circuitry controls the operation of the various coils 58, 62, 64 and the RF system, and signal-processing circuitry receives the output of the RF system, generating therefrom images of the patient supported by the couch 54.

As mentioned above, the system 50 further comprises a radiotherapy apparatus 66 which delivers doses of radiation to a patient supported by the couch 54. The majority of the radiotherapy apparatus 66, including at least a source of radiation 68 (e.g. an x-ray source and a linear accelerator) and a multi-leaf collimator (MLC) 70, is mounted on a chassis 72. The chassis 72 is continuously rotatable around the couch 54 when it is inserted into the treatment area, powered by one or more chassis motors. In the illustrated embodiment, a portal radiation detector 74 is also mounted on the chassis 72 opposite the radiation source 68 and with the rotational axis of the chassis positioned between them. The radiotherapy apparatus 66 further comprises control circuitry, which may be integrated within the system 50 shown in FIG. 3 or remote from it, and controls the radiation source 68, the MLC 70 and the chassis motor.

The radiation source 68 is positioned to emit a beam of radiation through the window defined by the two gradient coils 62, 64, and also through the window 60 defined in the primary magnet 58. The radiation beam may be a cone beam or a fan beam, for example.

In other embodiments, the radiotherapy apparatus 66 may comprise more than one source and more than one respective multi-leaf collimator.

In operation, a patient is placed on the couch 54 and the couch is inserted into the treatment area defined by the magnetic coils 62, 64 and the chassis 72. The control circuitry controls the radiation source 68, the MLC 70 and the chassis motor to deliver radiation to the patient through the window between the coils 62, 64. The chassis motor is controlled such that the chassis 72 rotates about the patient, meaning the radiation can be delivered from different directions. As in the first embodiment, the MLC 70 has a plurality of elongate leaves oriented orthogonal to the beam axis; an example is illustrated and described in our EP-A-0,314,214, the content of which is hereby incorporated by reference and to which the reader is directed in order to obtain a full understanding of the described embodiment. The leaves of the MLC 70 are controlled to take different positions blocking or allowing through some or all of the radiation beam, thereby altering the shape of the beam as it will reach the patient. Simultaneously with rotation of the chassis 72 about the patient, the couch 54 may be moved along a translation axis into or out of the treatment area (i.e. parallel to the axis of rotation of the chassis). With this simultaneous motion a helical radiation delivery pattern is achieved, known to produce high quality dose distributions.

Figure 4:
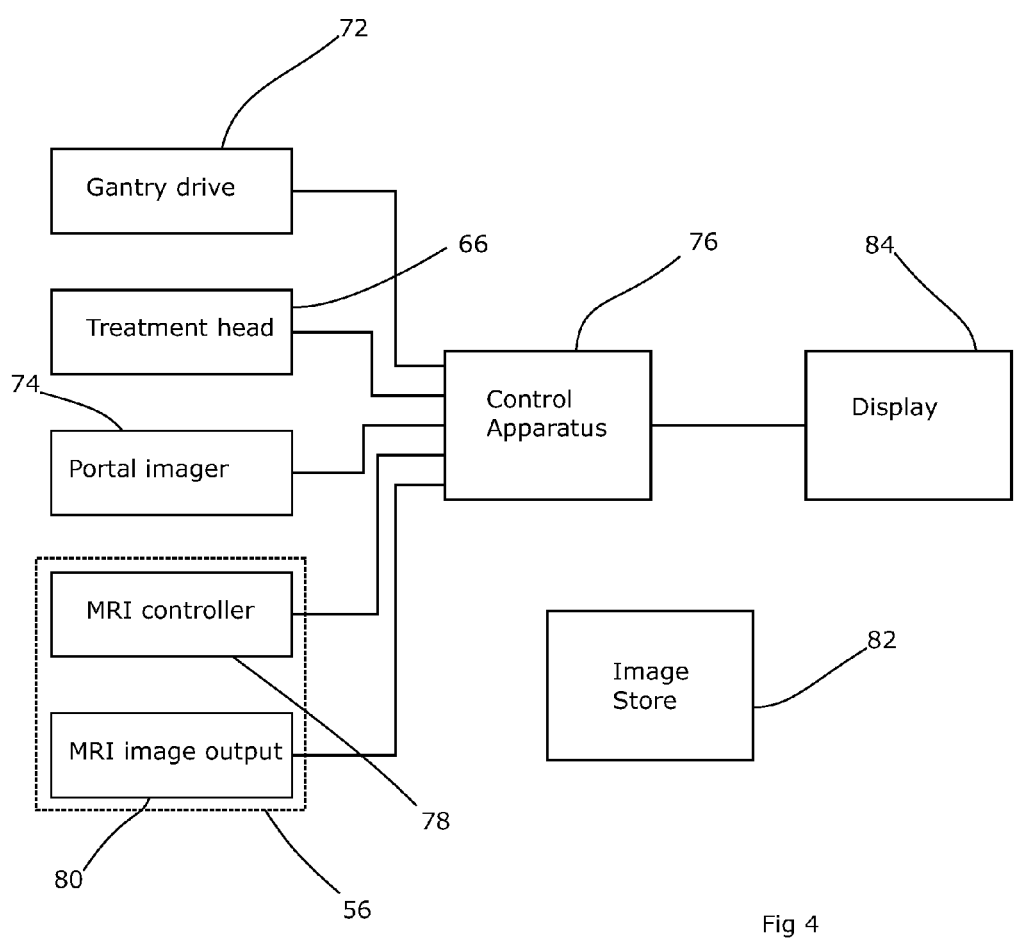
FIG. 4 shows a schematic functional structure for the apparatus of FIG. 2.

The MRI apparatus 56, and specifically the signal-processing circuitry, delivers real-time (or in practice near real-time) imaging data of the patient to the control circuitry. This information allows the control circuitry to adapt the operation of the MLC 70, for example, such that the radiation delivered to the patient accurately tracks the motion of the target region, for example due to breathing. It also allows a selected sectional image to be taken of the patient at a chosen point in time. Thus, with reference to FIG. 4, the control apparatus 76 instructs the MRI controller 78 within the MRI system 56 to capture a sectional image of the patient at the isocentre, oriented transverse to the instantaneous alignment of the treatment head 66 as dictated by the chassis drive 72. This sectional image can be captured by the MRI image output systems 80 (also within the MRI apparatus 56) and delivered to the control apparatus 76 which may place it in digital storage medium acting as an image store 82, if necessary. The control apparatus 76 also instructs the portal imager 74 to capture a portal image of the patient at substantially the same point in time, which may also be placed in the image store 82. In this way, the apparatus captures MRI and portal images of the patient that are synchronised in both direction and time.

When required, the control apparatus can fetch the MRI and portal images from the image store 82 and display them on a display 84 for a clinician to review. Alternatively, the control apparatus can display the latest image, in real or near-real time in which case the image store 82 will not be needed. The portal image that is displayed may, as before, be the actual portal image, or a dose image, or a gamma image, or another form of image derived from the portal imager 74.

Various modifications of this scheme may of course be made. For example, although we have described acquiring an MRI section that is simultaneous and aligned with the portal image, other imaging arrangements may be used. For example, the MRI system 56 could deliver a 3D (or 4D) volume image of the patient from which the desired sectional image could be extracted; this would eliminate the need to co-ordinate the MRI and radiotherapy systems with each other. The MRI system could (for example) simply provide a continuously-updating volume image instead. Alternatively, the portal images (or the dose images, or the gamma images etc) could be reconstructed into a volume image and displayed over the MRI volume image.

Figure 5:
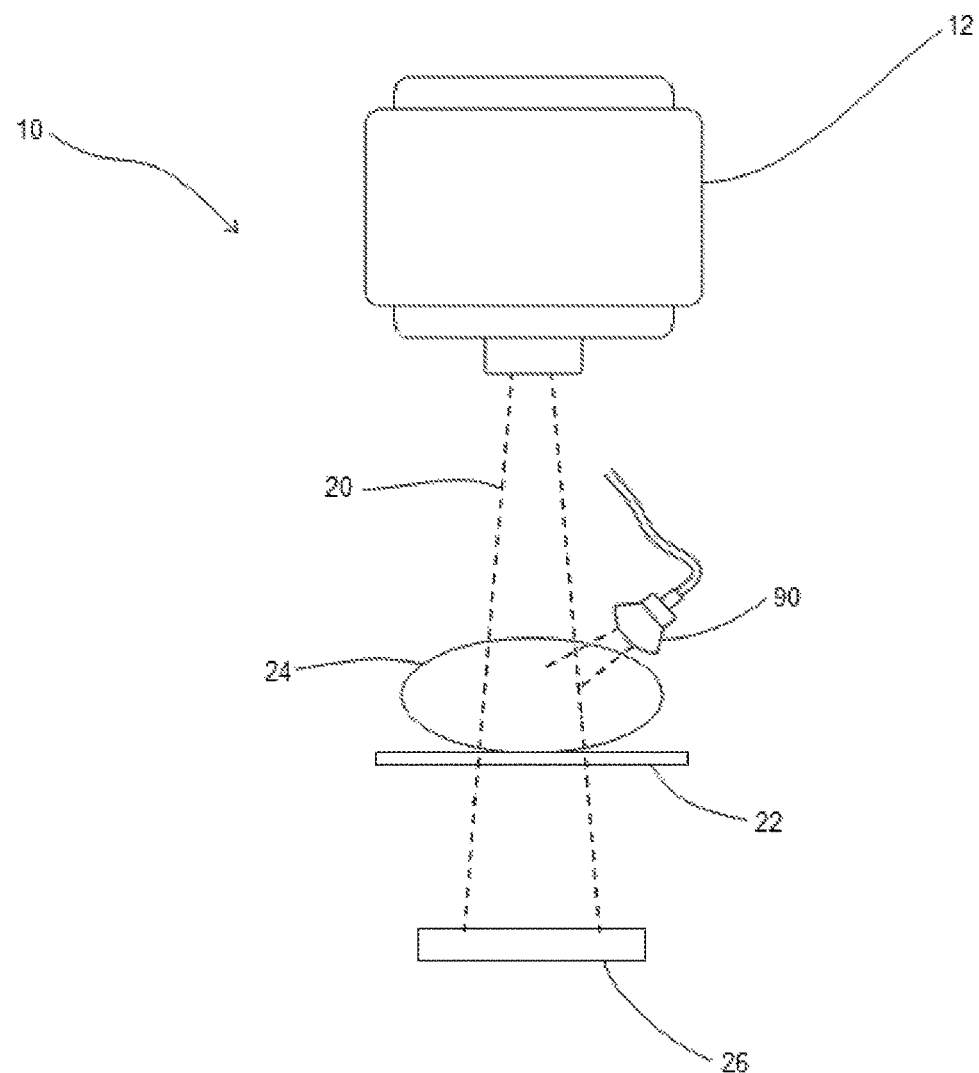
FIG. 5 shows a radiotherapy apparatus incorporating an ultrasound system as a second detector assembly.

Other imaging modalities could of course be used instead of the CT and MRI systems described herein. For example, ultrasound systems provide good, clear images with good contrast between tissue types and are therefore suitable for use with the present invention. FIG. 5 shows a radiotherapy apparatus 10 including therapeutic source 12 and EPID 26 positioned opposite the therapeutic source 12, on the other side of the patient support 22. This detects an image of the therapeutic x-ray beam 20 after it has been attenuated by the patient 24. An ultrasound system 90 functions as a second detector assembly and obtains diagnostic-quality images.

Figure 6:
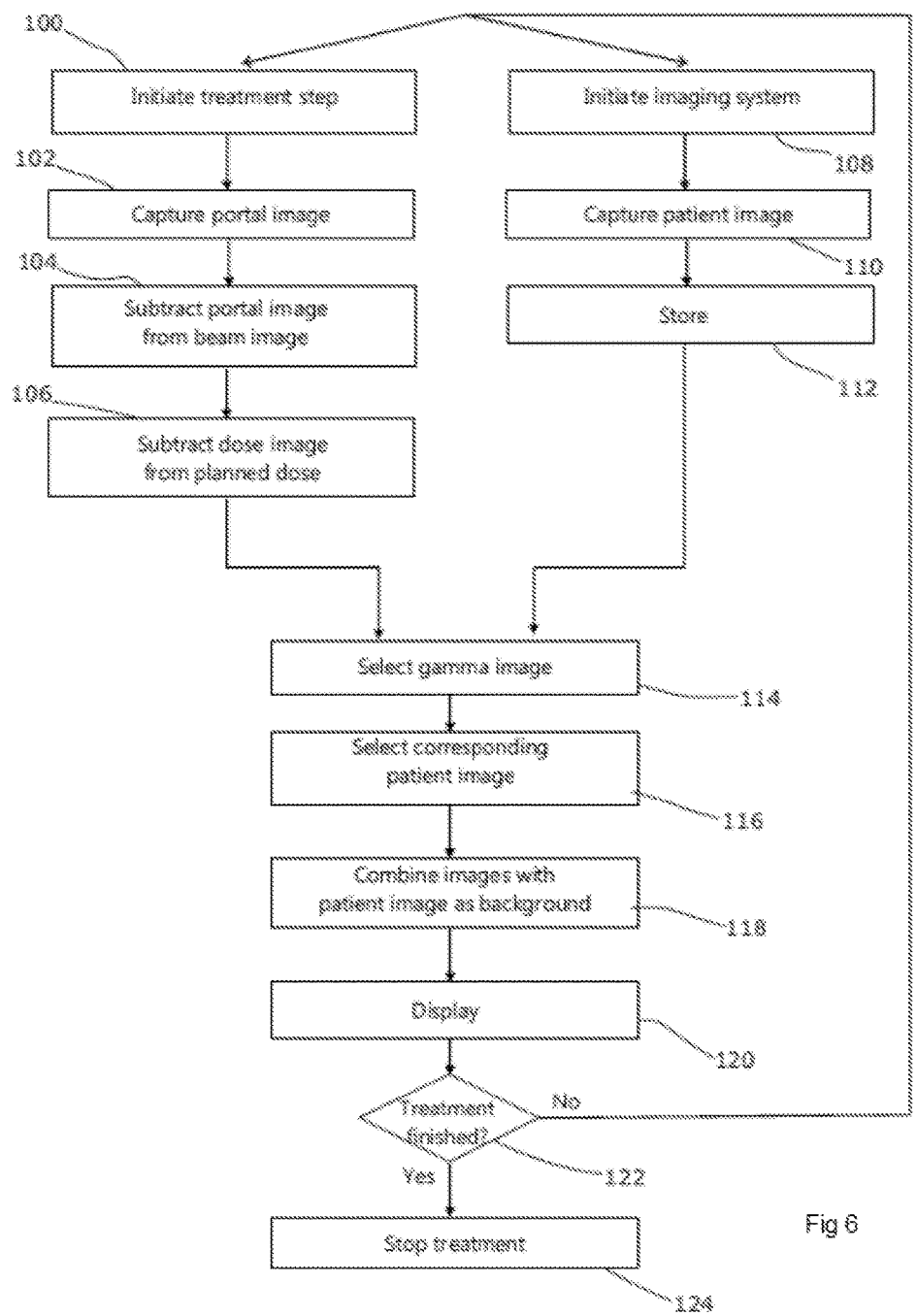
FIG. 6 shows a process flowchart for the present invention.

FIG. 6 shows a summary of the process that is adopted in the form of a flowchart. Starting at the top of the flowchart, there are two parallel processes running alongside each other. In the first process (to the left on FIG. 6), the system initiates a treatment step in box 100 which will involve directing therapeutic radiation towards the patient. A portal image is then captured (step 102) using this radiation as attenuated by the patient. The radiation that was emitted is a known, as this formed the basis of the instruction sent in step 100, so the portal image obtained in step 102 can be subtracted from that (step 104) to yield a dose image, i.e. an image of the dose pattern that was actually delivered in that step being the difference between the radiation that was sent towards the patient minus the radiation that passed through the patient and formed the portal image. The dose image can then be subtracted from the dose that was planned to be delivered (or vice-versa) to yield a gamma plot (step 106), i.e. a difference image showing discrepancies between the dose that was planned for and the dose that was actually received.

Meanwhile, the imaging system will have been initiated to ready it for the treatment step about to be delivered (step 108). At the necessary point, a patient image is captured (step 110). The manner in which the patient image is captured will depend on the nature of the imaging system (such as x-ray projection, CBCT, MRI, ultrasound etc) and the timing will depend on the geometry of the system in question, for example if the system depends on x-ray projection images taken with an angular offset. This image is then stored (step 112) if necessary.

To yield the viewable image, the gamma image is selected (step 114), as is the corresponding patient image (step 116). The two images are combined (step 118), with the patient image as a background to the gamma image. Alternatively, the images could be displayed side-by-side or otherwise in concert to allow comparison by a clinician. This is then displayed (step 120) for review.

If the treatment is still ongoing then the process can be repeated (step 122) to allow an ongoing near-real-time display of the treatment quality. Alternatively (or in addition), the images can be stored for later review. If the treatment is finished then the process can cease (step 124).

This process is of course simply one example of the various options, such as the selection of a gamma image rather than the portal image or dose image or a portal CT (etc).

It will of course be understood that many variations may be made to the above-described embodiments without departing from the scope of the present invention.

The invention claimed is:

1. A radiotherapy apparatus for providing radiation treatment to a patient, comprising:
   a source of therapeutic radiation;
   a first detector configured to detect the therapeutic radiation and generate a first detector output;
   a support configured to support the patient between the source and the first detector;
   a second detector assembly configured to derive an internal image of the patient on the support and to generate a second detector output; and
   a control apparatus configured to:
      receive the first and second detector outputs;
      reconstruct, from detector output information of only the first detector output, a volume image representing a radiation dose delivered to the patient by the source; and
      display the volume image against a background of an image derived from the second detector assembly.

2. The radiotherapy apparatus according to claim 1, wherein the source emits x-radiation at an energy of at least 1 MeV.

3. The radiotherapy apparatus according to claim 1, wherein the source comprises a linear accelerator.

4. The radiotherapy apparatus according to claim 1, wherein the first detector is a flat-panel scintillation detector.

5. The radiotherapy apparatus according to claim 1, wherein the volume image is a difference image showing a difference between a delivered dose derived from the first detector, and a previously-determined planned dose.

6. The radiotherapy apparatus according to claim 1, wherein the second detector assembly comprises a source of diagnostic radiation of lower energy than the therapeutic radiation, and a second detector for the diagnostic radiation.

7. The radiotherapy apparatus according to claim 6 in which the source of diagnostic radiation and the second detector are combined into a single unit.

8. The radiotherapy apparatus according to claim 1, wherein the second detector assembly comprises a magnetic-resonance imaging apparatus.

9. The radiotherapy apparatus according to claim 1, wherein the second detector assembly comprises an ultrasound apparatus.

10. The radiotherapy apparatus according to claim 1, wherein the image derived from the second detector assembly is a two-dimensional radiograph.

11. The radiotherapy apparatus according to claim 10, wherein the two-dimensional radiograph was obtained at a different time than that of the image derived from the first detector.

12. The radiotherapy apparatus according to claim 11, wherein the two-dimensional radiograph and the image are taken along substantially co-linear directions.

13. The radiotherapy apparatus according to claim 1, wherein the image derived from the second detector assembly is a section taken from a volume image created using the output of the second detector assembly.

14. The radiotherapy apparatus of claim 1, wherein the image derived from the second detector assembly is a section taken from one of a plurality of volume images created using the output of the second detector assembly, each depicting the patient at a different phase of a breathing cycle.

15. The radiotherapy apparatus according to claim 14, wherein the control apparatus is configured to select the volume image based on analysis of the image derived from the first detector.

16. The radiotherapy apparatus according to claim 1, wherein the image derived from the first detector is a two-dimensional radiograph.

17. A radiotherapy apparatus for providing radiation treatment to a patient, comprising:
   a first imaging system configured to direct therapeutic radiation toward the patient and to detect the therapeutic radiation after passing through the patient using only a first detector positioned downstream of the patient in a path of the therapeutic radiation;
   a second imaging system configured to;
      direct diagnostic radiation at lower energy than the therapeutic radiation toward the patient; and
      capture, using a second detector, an internal image of the patient after the diagnostic radiation passes through the patient; and
   a control apparatus configured to:
      reconstruct, using the detector output of only the first imaging system, a volume image representing a radiation dose delivered to the patient; and
      display the volume image against a background of an image derived from the second imaging system.

18. The radiotherapy apparatus according to claim 17, wherein the therapeutic radiation has an energy of at least 1 MeV.

19. The radiotherapy apparatus according to claim 17, wherein the control apparatus is configured to reconstruct the volume image using a computed tomography back projection technique.

20. A radiotherapy method for providing radiation therapy to a patient, comprising:
   receiving a first output from a first imaging system configured to direct therapeutic radiation toward the patient and to detect, using a first detector positioned downstream of the patient in a path of the therapeutic radiation, the therapeutic radiation after passing through the patient;
   reconstructing, based on a detector output of only the first output, a volume image representing a radiation dose delivered to the patient;
   receiving a second output from a second imaging system configured to:
      direct diagnostic radiation at lower energy than the therapeutic radiation toward the patient; and
      detect the diagnostic radiation after passing through the patient; and
   displaying the volume image against a background of an image derived from the second output.

21. The radiotherapy method of claim 20, wherein the image derived from the second output is a section taken from one of a plurality of volume images created using data corresponding to the detected diagnostic radiation.

* * * * *